(12) United States Patent
Toepke et al.

(10) Patent No.: US 9,703,279 B2
(45) Date of Patent: Jul. 11, 2017

(54) HANDHELD FIELD MAINTENANCE DEVICE WITH IMPROVED USER INTERFACE

(75) Inventors: Todd M. Toepke, Eden Prairie, MN (US); Christopher P. Kantzes, Minneapolis, MN (US); Brad N. Mathiowetz, Lakeville, MN (US); Kun Yang, Eden Prairie, MN (US); Adam E. Lund, St. Louis Park, MN (US)

(73) Assignee: Fisher-Rosemount Systems, Inc., Austin, TX (US)

( * ) Notice: Subject to any disclaimer, the term of this patent is extended or adjusted under 35 U.S.C. 154(b) by 699 days.

(21) Appl. No.: 13/191,634

(22) Filed: Jul. 27, 2011

(65) Prior Publication Data

US 2012/0038548 A1 Feb. 16, 2012

Related U.S. Application Data

(60) Provisional application No. 61/368,477, filed on Jul. 28, 2010.

(51) Int. Cl.
| | |
|---|---|
| *G06F 3/00* | (2006.01) |
| *G06F 3/048* | (2013.01) |
| *G05B 19/042* | (2006.01) |

(52) U.S. Cl.
CPC ....... *G05B 19/042* (2013.01); *G05B 19/0426* (2013.01); *G05B 2219/23018* (2013.01);
(Continued)

(58) Field of Classification Search
CPC .......... G06F 3/016; G06F 3/011; G06F 3/038; G06F 3/03543; G06F 3/0338;
(Continued)

(56) References Cited

U.S. PATENT DOCUMENTS

| | | | |
|---|---|---|---|
| 4,534,012 A | * | 8/1985 | Yokozawa .................... 368/327 |
| 5,195,392 A | | 3/1993 | Moore et al. ................ 73/866.5 |

(Continued)

FOREIGN PATENT DOCUMENTS

| | | |
|---|---|---|
| CN | 101763576 | 6/2010 |
| DE | 102007035158 | 1/2009 |

(Continued)

OTHER PUBLICATIONS

"Instruction Manual—Cond Transmitter 7100e FF", published to web on Jan. 27, 2003 at us.mt.com/dam/mt_ext_files/Editorial/Generic/3/BA_Conductivity_transmitter_Cond7100e_FF_Editorial_Generic_1102673421628_files/ba_conductivity_transmittercond7100effe52121253june05v2.pdf, retrieved Mar. 21, 2016.*

(Continued)

*Primary Examiner* — Doon Chow
*Assistant Examiner* — Shourjo Dasgupta
(74) *Attorney, Agent, or Firm* — Christopher R. Christenson; Kelly, Holt & Christenson, PLLC (57) ABSTRACT

A handheld field maintenance tool is provided. The handheld field maintenance tool includes a process communication module configured to communicate with a field device. The handheld field maintenance tool also includes a display and a user input device. A controller is coupled to the process communication module, the user input device and the display and is configured to generate a listing of task-based field maintenance operations on the display and receive a user input selecting a task-based field maintenance operation. The controller is configured to automatically traverse a menu of the field device using a fast-key sequence relative to the selected task. A method of creating a task-based field maintenance operation is provided. A method of interacting with a field device menu is also provided.

4 Claims, 7 Drawing Sheets

(52) U.S. Cl.
CPC ............ *G05B 2219/23054* (2013.01); *G05B 2219/23126* (2013.01); *G05B 2219/23163* (2013.01); *G05B 2219/23406* (2013.01); *G05B 2219/23445* (2013.01); *G05B 2219/23446* (2013.01); *G05B 2219/24001* (2013.01); *G05B 2219/24056* (2013.01); *G05B 2219/25062* (2013.01); *G05B 2219/25428* (2013.01); *G05B 2219/31121* (2013.01); *G05B 2219/31197* (2013.01); *G05B 2219/31475* (2013.01); *G05B 2219/32007* (2013.01); *G05B 2219/32144* (2013.01); *G05B 2219/32226* (2013.01); *G05B 2219/33331* (2013.01); *G05B 2219/35422* (2013.01); *G05B 2219/35429* (2013.01); *G05B 2219/36122* (2013.01); *G05B 2219/36128* (2013.01); *Y02P 90/14* (2015.11)

(58) Field of Classification Search
CPC .. G06F 3/0482; G06F 3/0481; G06F 3/04817; G06F 9/4443; H04N 5/44543
USPC ................. 345/156; 715/700, 733, 740, 748, 715/762–764, 810
See application file for complete search history.

(56) References Cited

U.S. PATENT DOCUMENTS

| | | | |
|---|---|---|---|
| 5,309,351 A | 5/1994 | McCain et al. | 364/132 |
| 5,442,632 A | 8/1995 | Burton et al. | 371/20.1 |
| 5,892,939 A * | 4/1999 | Call | G05B 19/0426 365/112 |
| 5,903,455 A | 5/1999 | Sharpe, Jr. et al. | 364/188 |
| 6,033,226 A | 3/2000 | Bullen | 434/219 |
| 6,211,649 B1 | 4/2001 | Matsuda | 320/115 |
| 6,236,223 B1 | 5/2001 | Brady et al. | 324/750.3 |
| 6,377,859 B1 | 4/2002 | Brown et al. | 700/79 |
| 6,629,059 B2 | 9/2003 | Borgeson et al. | 702/183 |
| 6,633,782 B1 | 10/2003 | Schleiss et al. | 700/26 |
| 6,725,182 B2 | 4/2004 | Pagnano et al. | 702/188 |
| 6,971,063 B1 | 11/2005 | Rappaport et al. | 715/733 |
| 7,013,184 B2 | 3/2006 | Romagnoli et al. | 700/17 |
| 7,117,122 B2 | 10/2006 | Zielinski et al. | 702/183 |
| 7,120,391 B2 | 10/2006 | Stengele et al. | 455/41.3 |
| 7,188,200 B2 | 3/2007 | Griech | 710/100 |
| 7,337,369 B2 | 2/2008 | Barthel et al. | 714/43 |
| 7,400,255 B2 | 7/2008 | Horch | 340/572.7 |
| 7,421,531 B2 | 9/2008 | Rotvold et al. | 710/315 |
| 7,454,252 B2 | 11/2008 | El-Sayed | 700/21 |
| 7,505,819 B2 | 3/2009 | El-Sayed | 700/21 |
| 7,506,812 B2 | 3/2009 | von Mueller et al. | 235/449 |
| 7,675,406 B2 | 3/2010 | Baier et al. | 340/506 |
| 7,733,833 B2 | 6/2010 | Kalika et al. | 370/338 |
| 7,797,061 B2 | 9/2010 | El-Sayed | 700/21 |
| 8,000,815 B2 | 8/2011 | John et al. | 700/18 |
| 8,036,007 B2 | 10/2011 | Woehrle | 363/65 |
| 8,059,101 B2 | 11/2011 | Westerman et al. | 345/173 |
| 8,060,862 B2 | 11/2011 | Eldridge et al. | 717/121 |
| 8,060,872 B2 | 11/2011 | Da Silva Neto | 717/177 |
| 8,074,172 B2 | 12/2011 | Kocienda et al. | 715/263 |
| 8,126,145 B1 | 2/2012 | Tewari et al. | 380/255 |
| 8,150,462 B2 | 4/2012 | Guenter et al. | 455/557 |
| 8,180,948 B2 | 5/2012 | Kreider et al. | 710/313 |
| 8,224,256 B2 | 7/2012 | Citrano, III et al. | 455/67.11 |
| 8,677,262 B2 * | 3/2014 | Baier et al. | 715/772 |
| 2001/0047504 A1 | 11/2001 | Aoyama | 714/799 |
| 2002/0004370 A1 | 1/2002 | Stengele et al. | 455/39 |
| 2002/0007237 A1 | 1/2002 | Phung et al. | 701/33 |
| 2002/0027504 A1 | 3/2002 | Davis et al. | 340/540 |
| 2002/0080157 A1 * | 6/2002 | Chickles | G06F 8/34 715/700 |
| 2002/0086642 A1 | 7/2002 | Ou et al. | 455/69 |
| 2002/0167904 A1 | 11/2002 | Borgeson et al. | 702/183 |
| 2002/0171558 A1 | 11/2002 | Bartelheim et al. | 340/825.49 |
| 2003/0050737 A1 | 3/2003 | Osann, Jr. | 700/276 |
| 2003/0109937 A1 | 6/2003 | Zielinski et al. | 700/1 |
| 2003/0119561 A1 * | 6/2003 | Hatch | H04M 1/274525 455/566 |
| 2003/0204373 A1 | 10/2003 | Zielinski et al. | 702/184 |
| 2003/0229472 A1 | 12/2003 | Kantzes et al. | 702/183 |
| 2004/0004598 A1 * | 1/2004 | Muthuswamy et al. | 345/156 |
| 2004/0039458 A1 | 2/2004 | Mathiowetz et al. | 700/17 |
| 2004/0111238 A1 | 6/2004 | Kantzes et al. | 702/183 |
| 2004/0193287 A1 | 9/2004 | Lefebvre et al. | 700/1 |
| 2004/0204193 A1 | 10/2004 | Li et al. | 455/575.1 |
| 2004/0228184 A1 | 11/2004 | Mathiowetz | 365/202 |
| 2004/0230327 A1 | 11/2004 | Opheim et al. | 700/83 |
| 2005/0078968 A1 * | 4/2005 | Ohta | 399/8 |
| 2005/0114086 A1 | 5/2005 | Zielinski et al. | 702/183 |
| 2005/0164684 A1 | 7/2005 | Chen et al. | 455/414.1 |
| 2005/0222698 A1 | 10/2005 | Eryurek et al. | 700/90 |
| 2005/0223120 A1 | 10/2005 | Scharold et al. | 710/1 |
| 2006/0014533 A1 | 1/2006 | Warren | 455/423 |
| 2006/0087402 A1 | 4/2006 | Manning et al. | 340/3.1 |
| 2006/0155908 A1 | 7/2006 | Rotvold et al. | 710/315 |
| 2006/0181510 A1 * | 8/2006 | Faith | G06F 1/1626 345/158 |
| 2006/0206277 A1 | 9/2006 | Horch | 702/82 |
| 2006/0290496 A1 | 12/2006 | Peeters | 340/572.1 |
| 2006/0291438 A1 | 12/2006 | Karschnia et al. | 370/338 |
| 2007/0038730 A1 * | 2/2007 | Dietrich et al. | 709/220 |
| 2007/0161352 A1 | 7/2007 | Dobrowski et al. | 455/69 |
| 2007/0161371 A1 | 7/2007 | Dobrowski et al. | 455/423 |
| 2007/0179645 A1 | 8/2007 | Nixon et al. | 700/83 |
| 2007/0180407 A1 * | 8/2007 | Vahtola | 715/847 |
| 2007/0208279 A1 | 9/2007 | Panella et al. | 600/595 |
| 2007/0240065 A1 * | 10/2007 | Alperin | G06F 17/30867 715/745 |
| 2008/0114911 A1 | 5/2008 | Schumacher | 710/72 |
| 2008/0222565 A1 * | 9/2008 | Taylor et al. | 715/810 |
| 2008/0234837 A1 | 9/2008 | Samudrala et al. | 700/19 |
| 2008/0268784 A1 * | 10/2008 | Kantzes | G05B 19/0423 455/66.1 |
| 2009/0065578 A1 | 3/2009 | Peterson et al. | 235/382 |
| 2009/0066527 A1 * | 3/2009 | Teachman | G01R 22/10 340/657 |
| 2009/0094466 A1 | 4/2009 | Matthew et al. | 713/300 |
| 2009/0125713 A1 | 5/2009 | Karschnia et al. | 713/153 |
| 2009/0171483 A1 | 7/2009 | Scheuermann | 700/83 |
| 2009/0177970 A1 | 7/2009 | Jahl et al. | 715/735 |
| 2009/0271726 A1 | 10/2009 | Gavimath et al. | 715/771 |
| 2009/0284390 A1 | 11/2009 | Lahner et al. | 340/825.49 |
| 2009/0296601 A1 | 12/2009 | Citrano et al. | 370/254 |
| 2009/0297062 A1 * | 12/2009 | Molne | G06F 3/0304 382/289 |
| 2009/0305727 A1 * | 12/2009 | Pylkko | G06F 1/1626 455/456.3 |
| 2009/0326852 A1 | 12/2009 | Vetter et al. | 702/108 |
| 2010/0023140 A1 | 1/2010 | Kodama et al. | |
| 2010/0100766 A1 | 4/2010 | Bengtsson et al. | 714/23 |
| 2010/0114347 A1 | 5/2010 | Dheenathayalan et al. | 700/97 |
| 2010/0114549 A1 | 5/2010 | Kolavi | 703/13 |
| 2010/0145476 A1 | 6/2010 | Junk et al. | 700/7 |
| 2010/0220630 A1 | 9/2010 | Kalika et al. | 370/254 |
| 2010/0290084 A1 | 11/2010 | Russell, III et al. | 358/1.15 |
| 2010/0290351 A1 | 11/2010 | Toepke et al. | 370/250 |
| 2010/0290359 A1 | 11/2010 | Dewey et al. | 370/252 |
| 2010/0293363 A1 | 11/2010 | Meyer et al. | 713/1 |
| 2011/0072338 A1 * | 3/2011 | Caldwell | G05B 19/41845 715/205 |
| 2011/0117529 A1 | 5/2011 | Barash et al. | 434/265 |
| 2011/0238188 A1 | 9/2011 | Washiro | 700/19 |
| 2012/0038458 A1 | 2/2012 | Toepke et al. | 340/6.1 |
| 2012/0038760 A1 | 2/2012 | Kantzes et al. | 348/61 |
| 2012/0040316 A1 | 2/2012 | Mathiowetz et al. | 434/219 |
| 2012/0040698 A1 | 2/2012 | Ferguson et al. | 455/457 |
| 2012/0041744 A1 | 2/2012 | Kantzes et al. | 703/13 |
| 2012/0046911 A1 | 2/2012 | Mathiowetz et al. | 702/184 |

FOREIGN PATENT DOCUMENTS

| | | |
|---|---|---|
| EP | 1515208 | 3/2005 |
| EP | 1916582 | 4/2008 |

(56) References Cited

FOREIGN PATENT DOCUMENTS

| | | |
|---|---|---|
| EP | 2071427 | 6/2009 |
| EP | 2077473 | 7/2009 |
| EP | 2148259 | 1/2010 |
| EP | 2204705 | 7/2010 |
| GB | 2382418 | 5/2003 |
| GB | 2 394 124 | 4/2004 |
| JP | 9051583 | 2/1997 |
| JP | 2001337004 | 7/2001 |
| JP | 2001337004 | 12/2001 |
| JP | 2008165193 | 7/2008 |
| KR | 20060078883 | 7/2006 |
| WO | WO 01/35190 | 5/2001 |
| WO | WO 02/086662 | 10/2002 |
| WO | WO 2008/096216 | 3/2003 |
| WO | WO 2006/016845 | 2/2006 |
| WO | WO 2007003187 A1 | 1/2007 |
| WO | WO 2008/042074 | 4/2008 |
| WO | WO 2008/077358 | 7/2008 |
| WO | WO 2008/096216 | 8/2008 |
| WO | WO 2008/127632 | 10/2008 |
| WO | WO 2009/003146 | 12/2008 |
| WO | WO 2009/003148 | 12/2008 |
| WO | WO 2009/074544 | 6/2009 |

OTHER PUBLICATIONS

1420 Wireless Gateway. Reference. Manual 00809-0100-4420, Rev BA. Aug. 2007. Emerson Process Management.
First Office Action from related Japanese application No. 2015511048, dated Jan. 29, 2011.
Lee S W et al: "Honam Petrochemical Corporation Uses Simulator for Ethylene Plant Operator Training", Processing of the Industrial Computing Conference. Houston, Oct. 18-23, 1992, pp. 219-222.
Kurrle H-P et al.: "Trainingssimulator Zur Ausbildung Von Chemikanten und Anlagenfahrern. Otraining Simulator for the Training of Process Workers (Chemikanten) and Operators". Automatisierungstechnische Praxis—ATP, Oldenbourg Indusrieverlag, Munchen, DE, vol. 36, No. 7, Jul. 1, 1994. Abstract, Section 2.
Bushman J B: "Ally: An Operator's Associate for Cooperative Supervisory Control Systems", IEEE Transactions on Systems, Man and Cybernetics, IEEE Inc. New York, US, vol. 23, No. 1, Jan. 1, 1993, pp. 111-128.
Invitation to Pay Additional Fees for international patent application No. PCT/US2010/034889 dated Sep. 15, 2010.
ABB Limited: "Wireless Instrumentation Jargon Buster". Information bulletin instrumentation ABB No. IB/INST-018, Mar. 3, 2009, XP002596601. Retrieved from the Internet: URL:http://www05.abb.com/global/scot/scot203.nsf/veritydisplay/be00ec76ef07e978c125756e003157b9/$File/IB_INST_018_1.pdf.
Notification of Transmittal of the International Search Report and the Written Opinion from the International Application No. PCT/US2010/021764.
David Gustafsson: "WirelessHART—Implementation and Evaluation on Wireless Sensors". Masters's Degree Project, KTH University, Electrical Engineering, Apr. 1, 2009, pp. 1-39, XP002596602, Stockholm, Sweden. Retrieved from the Internet: URL:http://www.ee.kth.se/php/modules/publications/reports/2009/XR-EE-RT %202009:003.pdf.
Notification of Transmittal of the International Search Report and the Written Opinion for the International application No. PCT/US2010/034848 dated Aug. 26, 2010.
Possio Bluetooth to WLAN Gateway PX20: Full Product Description retrieved from http://www.blueunplugged.com/p.aspx?p=105816.
1420 Wireless Gateway: Product Data Sheet 00813-0100-4420, Rev BA Mar. 2008. Emerson Process Management.
Smart Wireless Gateway (WirelessHART™). Quick Installation Guide 00825-0200-4420, Rev BA. Aug. 2009. Emerson Process Management.
Rosemount 3051S Wireless Series Scalable Pressure, Flow, and Level Solutions. Reference Manual 00809-0100-4802, rev BA. Aug. 2007. Emerson Process Management.
EPO Communication pursuant to Rules 161(1) and 162 EPC for European patent application No. 10701430.0 dated Aug. 30, 2011.
Invitation to Pay Additional Fees for international patent application No. PCT/US2010/034949 dated Sep. 17, 2010.
Technical Data Sheet: VIATOR® USB HART® Interface (Model 010031). MACTek Measurement and Control Technologies.
Viator® Bluetooth® Wireless Technology Interface for use with HART field devices. MACTek Measurement and Control Technologies retrieved from www.mactekcorp.com/product5.htm.
Product Data Sheet: VIATOR RS232. MACTek Measurement and Control Technologies retrieved from www.mactekcorp.com/product1.htm.
Notification of Transmittal of the International Search Report and the Written Opinion from the International Application No. PCT/US2010/034889.
Notification of Transmittal of the International Search Report and the Written Opinion from the International Application No. PCT/US2010/034949.
EPO Communication from related European application No. 10730279.6 dated Jan. 13, 2012.
EPO Communication from related European application No. 10730281.2 dated Jan. 13, 2012.
EPO Communication from related European application No. 10725543.2 dated Jan. 12, 2012.
Rosemount 3051SMV Quick Installation Guide 00825-0100-4803 Rev BA. Apr. 2011.
Invitation to Pay Additional Fees from the International Application No. PCT/US2011/045673 dated Jan. 16, 2012.
Notification of Transmittal of the International Search Report and the Written Opinion from the International Application No. PCT/US2011/045680 dated Jul. 6, 2012.
Notification of Transmittal of the International Search Report and the Written Opinion from the International Application No. PCT/US2011/045681 dated Jan. 5, 2012.
475 Field Communicator. User's Guide XP007919976. Aug. 2009. www.fieldcommunicator.com by Emerson Process Management.
First Office Action from counterpart Japanese patent application No. 2013-521963, dispatched Feb. 4, 2014. 10 Pages.
Rosemount 3051 Pressure Transmitter, U.S. EMERSON, Jan. 5, 2007, Reference Manual 00809-0100-4051, RevAA, 3-6, <<http://www2.emersonprocess.com/siteadmincenter/PM%20Rosemount %20Documents/00809-0100-4051.pdf >> 164 Pages.
First Office Action from Chinese Counterpart Application No. 201180001612.7 dated Oct. 10, 2014. 9 pages.
Notification on the results of patentability check from Russian counterpart Application No. 2013108826, dated Oct. 9, 2014, 10 pages.
Rosemount 3051 Pressure Transmitter, U.S. EMERSON, Jan. 5, 2007, Reference Manual 00809-0100-4051, RevAA, 3-6, << http://www2.emersonprocess.com/siteadmincenter/PM%20Rosemount %20Documents/00809-0100-4051.pdf >> 164 Pages.
Rosemount 3051 Pressure Transmitter, U.S. Emerson, Jan. 5, 2007, Reference Manual 00809-0100-4051, RevAA. 3-6, << http://www2.emersonprocess.com/siteadmincenter/PM%20Rosemount %20Documents/00809-0100-4051.pdf >> 164 Pages.
Office Action from Canadian patent application No. 2,806,946 dated Jul. 28, 2014. 3 pages.
Office Action from Russian patent application No. 2013108826 dated May 21, 2014. 6 pages with English translation.
Office Action dated Oct. 2, 2015 from Canadian patent application No. 2,806,946. 4 pages.
1420 Wireless Gateway. Reference Manual 00809-0100-4420, Rev BA. Aug. 2007. Emerson Process Management.
Invitation to pay additional fees from the related International patent application No. PCT/US2011/045679 dated Aug. 6, 2012.
Invitation to pay additional fees from the related International patent application No. PCT/US2011/045664 dated Aug. 9, 2012.
Invitation to pay additional fees from the related International patent application No. PCT/US2011/045676 dated Jul. 30, 2012.

(56) References Cited

OTHER PUBLICATIONS

First Communication from related European patent application No. 107302796 dated Oct. 19, 2012.
Office Action from related Russian application No. 2011151063 dated Nov. 12, 2012.
First Office Action from related Japanese application No. 201511048, dated Jan. 29, 2013.
Lee S W et al: "Honam Petrochemical Corporation Uses Simulator for Ethylene Plant Operator Training", Processing of the Industrial Computing Conference. Houston, Oct. 18-23, 1992. pp. 219-222.
Kurrle H-P et al.: "Trainingssimulator Zur Ausbildung Von Chemikanten und Anlagenfahrern. Otraining Simulator for the Training of Process Workers (Chemikanten) and Operators". Automatisierungstechnische Praxis—ATP, Oldenbourg Indusrieverlag, Munchen. DE, vol. 36, No. 7. Jul. 1, 1994. Abstract, Section 2.
Invitation to pay additional fees from the related International patent application No. PCT/US2011/045665 dated Aug. 23, 2012.
Bushman J B: "Ally: An Operator's Associate for Cooperative Supervisory Control Systems", IEEE Transactions on Systems. Man and Cybernetics. IEEE Inc. New York, US, vol. 23. No. 1. Jan. 1, 1993, pp. 111-128.
First Communication for the related European patent application No. 107302812 dated Oct. 11, 2012.
International Search Report and Written Opinion from the related International patent application No. PCT/US2011/045664 dated Nov. 6, 2012.
International Search Report and Written Opinion from the related International patent application No. PCT/US2011/045679 dated Nov. 6, 2012.
International Search Report and Written Opinion from the related International patent application No. PCT/US2011/045665 dated Nov. 6, 2012.
First Communication from related European patent application No. 107255432 dated Oct. 11, 2012.

\* cited by examiner

HANDHELD FIELD MAINTENANCE DEVICE WITH IMPROVED USER INTERFACE

CROSS-REFERENCE TO RELATED APPLICATION

The present application is based on and claims the benefit of U.S. provisional patent application Ser. No. 61/368,477, filed Jul. 28, 2010, the content of which is hereby incorporated by reference in its entirety.

BACKGROUND

Handheld field maintenance tools are known. Such tools are highly useful in the process control and measurement industry to allow operators to conveniently communicate with and/or interrogate field devices in a given process installation. Examples of such process installations include petroleum, pharmaceutical, chemical, pulp, and other fluid processing installations. In such installations, the process control and measurement network may include tens or even hundreds of various field devices which periodically require maintenance to ensure that such devices are functioning properly and/or calibrated. Moreover, when one or more errors in the process control and measurement installation are detected, the use of a handheld field maintenance tool allows a technician to quickly diagnose such errors in the field. Handheld field maintenance tools are generally used to configure, calibrate, and diagnose problems relative to intelligent field devices using digital process communication protocols.

Since at least some process installations may involve highly volatile, or even explosive, environments, it is often beneficial, or even required, for field devices and the handheld field maintenance tools used with such field devices to comply with intrinsic safety requirements. These requirements help ensure that compliant electrical devices will not generate a source of ignition even under fault conditions. One example of Intrinsic Safety requirements is set forth in: APPROVAL STANDARD INTRINSICALLY SAFE APPARATUS AND ASSOCIATED APPARATUS FOR USE IN CLASS I, II and III, DIVISION NUMBER 1 HAZARDOUS (CLASSIFIED) LOCATIONS, CLASS NUMBER 3610, promulgated by Factory Mutual Research October, 1998. An example of a handheld field maintenance tool that complies with intrinsic safety requirements includes that sold under trade designation Model 475 Field Communicator, available from Emerson Process Management of Austin, Tex.

SUMMARY

A handheld field maintenance tool is provided. The handheld field maintenance tool includes a process communication module configured to communicate with a field device. The handheld field maintenance tool also includes a display and a user input device. A controller is coupled to the process communication module, the user input device and the display and is configured to generate a listing of task-based field maintenance operations on the display and receive a user input selecting a task-based field maintenance operation. The controller is configured to automatically traverse a menu of the field device using a fast-key sequence relative to the selected task. A method of creating a task-based field maintenance operation is provided. A method of interacting with a field device menu is also provided.

DETAILED DESCRIPTION

Figure 1A:
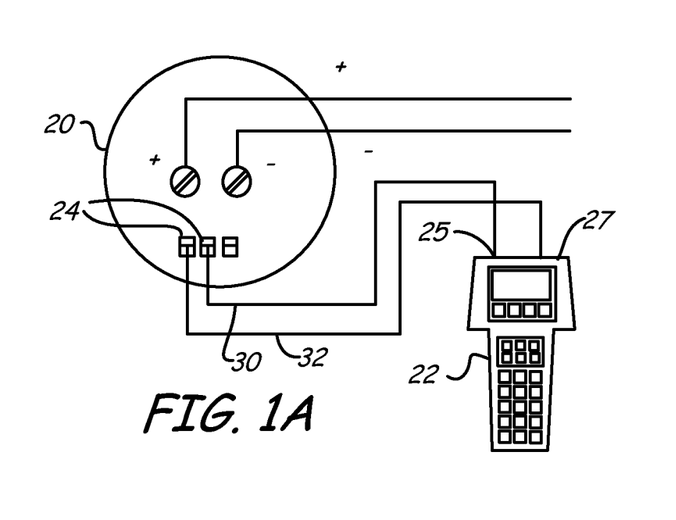
FIGS. 1A and 1B are diagrammatic views of a handheld field maintenance tool with which embodiments of the invention are particularly useful.
Figure 1B:
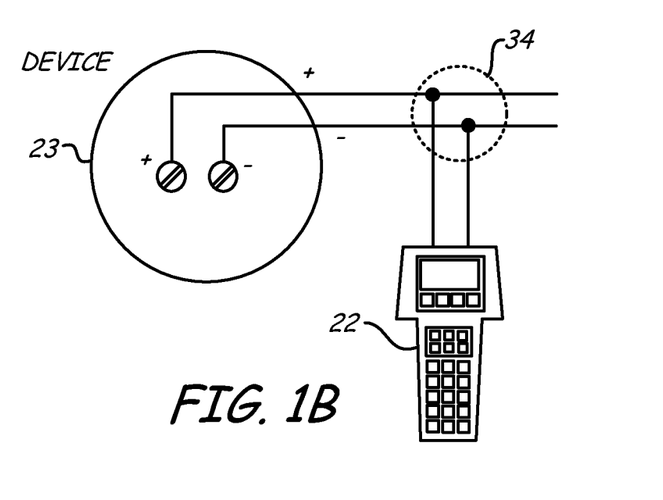

FIGS. 1A and 1B are diagrammatic views of a handheld field maintenance tool 22 coupled to field devices 20, 23. As shown in FIG. 1A, handheld field maintenance tool 22 includes a pair of terminals 25, 27 that couple to test leads 30, 32, respectively, which are then coupled to terminals 24 of field device 20. Terminals 24 may be dedicated terminals to allow such a handheld field maintenance tool to couple to device 20 and interact with device 20. The utilization of terminals 25, 27 to couple to field device illustrates an example of a wired connection between handheld field maintenance tool 22 and field device 20.

FIG. 1B shows an alternate arrangement where handheld field maintenance tool 22 couples directly to the process control loop 34 to which field device 23 is coupled. In either case, the wired connection between the handheld field maintenance tool and the field device allows the handheld field maintenance tool to interact with the desired field device 20, 23.

Figure 2:
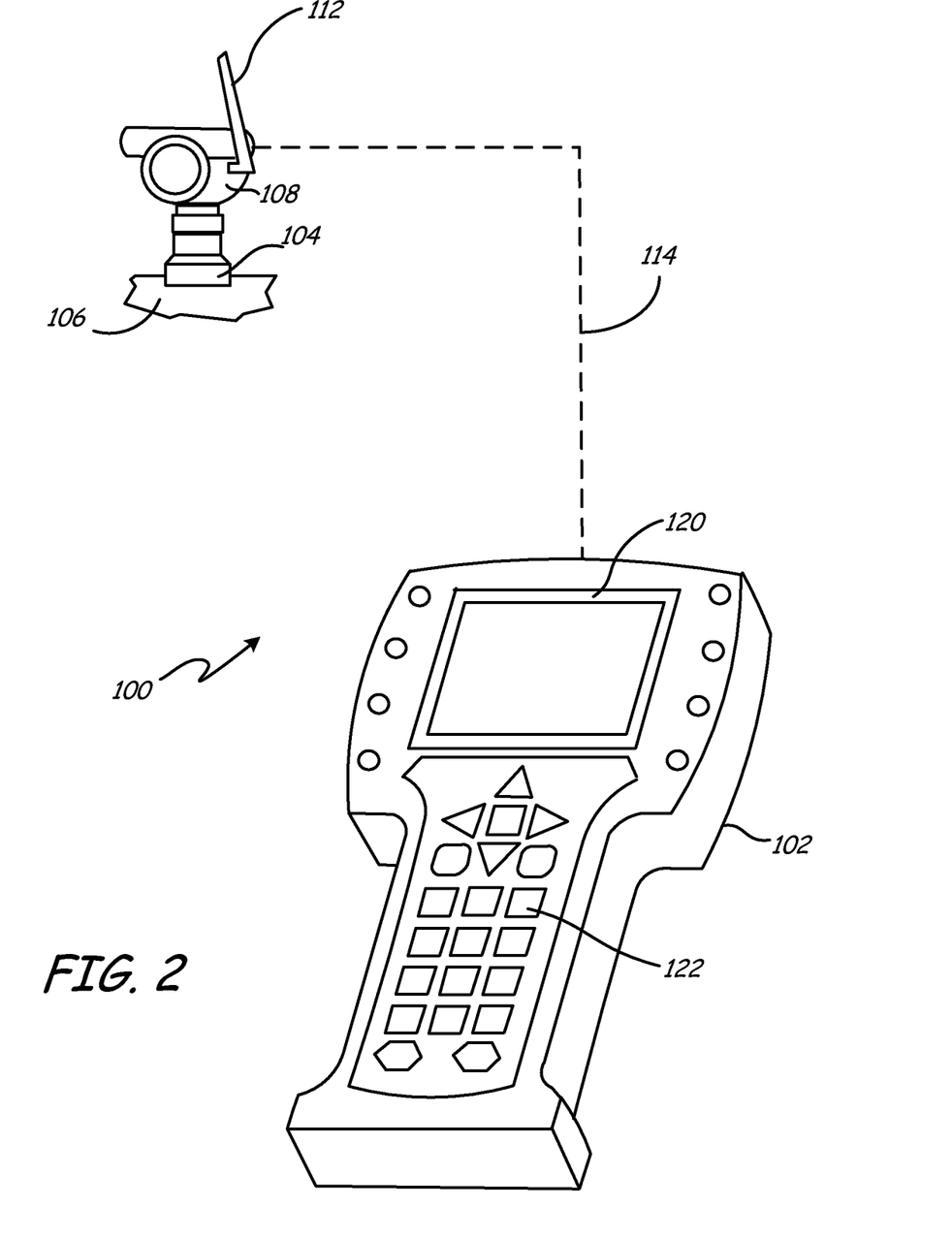
FIG. 2 is a diagrammatic view of a handheld field maintenance tool with which embodiments of the present invention are particularly useful.

FIG. 2 is a diagrammatic view of handheld field maintenance tool 102 interacting with wireless field device 104. System 100 includes handheld field maintenance tool 102 communicating with field device 104. Handheld field maintenance tool 102 is communicatively coupled to field device 104 via communication link 114. Communication link 114 can take any suitable form including wired connections as shown in FIGS. 1A and 1B, as well as wireless communication techniques that are currently being used or being developed. Handheld field maintenance tool 102 allows a technician to interact with field device 104 to configure, calibrate, and/or diagnose problems with respect to field device 104 using a digital process communication protocol such as FOUNDATION™ Fieldbus, Profibus, and/or the HART® protocol. Handheld field maintenance tools, such as tool 102 can be used to save configuration data from field devices, such as field device 104.

Field device 104 may be any device that senses a variable in the process and transmits information related to the variable over a process communication loop; such as a pressure or temperature. Field device 104 may also be a device that receives information from a process communication loop and sets a physical parameter, such as a valve closure, based on the information. Field device 104 is depicted as an industrial process fluid pressure transmitter having a pressure manifold 106 coupled thereto, and an electronics enclosure 108. Field device 104 is provided for illustrative purposes only. In reality, field device 104 may be any industrial device, such as a process fluid temperature transmitter, process fluid level transmitter, process fluid flow transmitter, valve controller, or any other device that is useful in the measurement and/or control of industrial processes.

Handheld field maintenance tool 102 generally includes a user interface that comprises a display 120 as well as a number of user input buttons 122. Display 120 may be any suitable display such as an active-matrix liquid crystal display, or any other suitable display that is able to provide useful information. Buttons 122 may comprise any suitable arrangement of buttons relative to any number of functions to which the handheld field maintenance tool may be directed. Buttons 122 may comprise a numeric keypad, an alphanumeric keypad, any suitable number of custom functions and/or navigation buttons, or any combination thereof.

Figure 3:
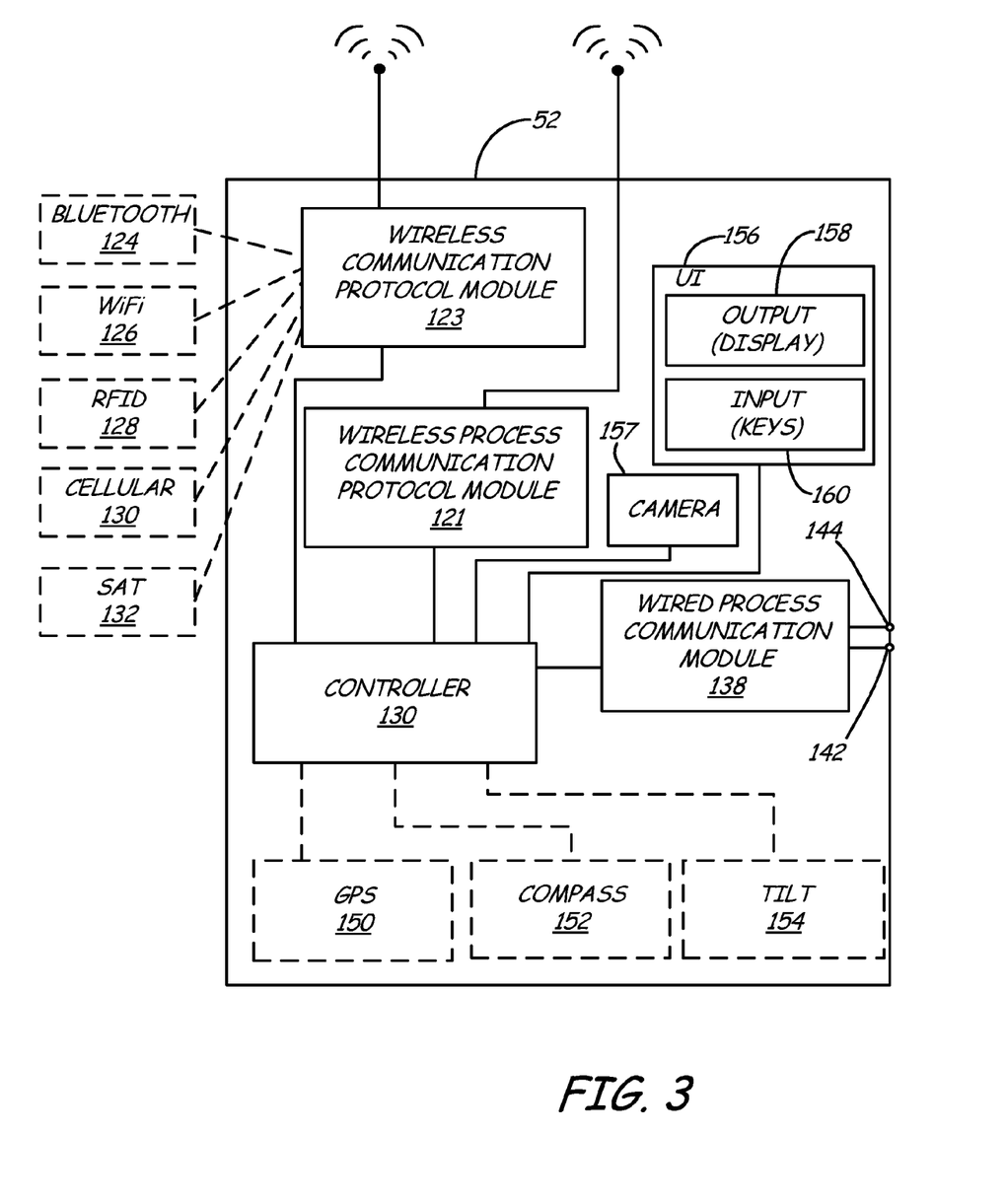
FIG. 3 is a diagrammatic system block diagram of a handheld field maintenance tool in accordance with an embodiment of the present invention.

FIG. 3 is a diagrammatic system block diagram of a handheld field maintenance tool in accordance with the embodiment of the present invention. It is preferred that tool 52 comply with at least one intrinsic safety specification, such as that listed above, in order to help ensure safety in potentially explosive environments. Handheld field maintenance tool 52 includes at least one wireless process communication module 121. Suitable examples for wireless process communication module 121 include a module that generates and/or receives proper signals in accordance with a known wireless communication protocol, such as the known WirelessHART protocol (IEC 62591). Another wireless process communication protocol is set forth in ISA100.11a. While FIG. 3 shows a single wireless process communication module 121, it is expressly contemplated that any suitable number of wireless process communication modules can be used to communicate in accordance with various wireless process communication protocols now in existence or later developed.

Handheld field maintenance tool 52 also includes at least one secondary wireless communication protocol module 123. Wireless communication protocol module 123 can communicate in accordance with one or more of the options shown in phantom in FIG. 3. Specifically, wireless communication protocol module 123 may communicate in accordance with a Bluetooth specification 124 (such as Bluetooth Specification 2.1 rated at Power Class 2; a Wi-Fi specification 126 (such as IEEE 802.11.a/b/g/n); a known RFID specification 128; cellular communication techniques 130 (such as GSM/CDMA); and/or satellite communication 132. These communication techniques and methodologies allow handheld field maintenance tool 52 to communicate directly with a wireless gateway or other suitable device either via direct wireless communication, or using the Internet. While one wireless communication protocol module 123 is shown in FIG. 3, any suitable number may be used. Each of the wireless process communication protocol module 121 and wireless communication protocol module 123 is coupled to controller 130 which is also coupled to the wired process communication module 138. Controller 130 is preferably a microprocessor that executes a sequence of instructions stored therein, or in memory coupled to controller 130, to perform handheld field maintenance tasks. Wired process communication module 138 allows handheld field maintenance tool 52 to be physically coupled via a wired connection at terminals 142, 144 to a field device. Examples of suitable wired process communication include the highway addressable remote transducer (HART®) protocol, the FOUNDATION™ Fieldbus protocol, Profibus and others.

Handheld field maintenance tool 52 includes a user interface module 156 for generating a user interface using display 120 and keys 122. Module 156 can include suitable display driver circuitry 158 and/or memory to interact with display 120. Module 156 also includes input circuitry 160 which is configured to interact with buttons 122 to receive user input. Additionally, in embodiments where display 120 includes a touchscreen, module 160 can include circuitry to generate user input data to controller 130 based upon a user's touch and/or gestures received by the touchscreen.

Handheld field maintenance tool 52 can include a number of additional items that facilitate additional functionality. Specifically, tool 52 can include a position detection module, such as GPS module 150. GPS module 150 can be configured to additionally use the Wide Area Augmentation System (WAAS) for improved accuracy and/or can be configured to operate using differential GPS techniques as appropriate. Module 150 is coupled to controller 130 to provide controller 130 with an indication of the geographic position of tool 52. While position detection module 150 is preferably an internal component of tool 52, it may be external and communicatively coupled thereto using a suitable wireless or wired communication protocol, such as Bluetooth 124, RFID 128, et cetera. Further still, while position detection module 150 is generally described as GPS module 150, other techniques for triangulating the position of the handheld field maintenance tool based upon relative strength of wireless communication with wireless transceivers having known fixed positions can be employed. Examples of such wireless triangulation techniques include triangulation of the position of handheld field maintenance tool 52 based upon communication with three or more fixed-position WiFi communication points, or access points. Further still, as set forth above, embodiments of the present invention may include the ability to employ one or more wireless process communication protocol modules, such as module 121. Such triangulation techniques can also be employed if a suitable number of wireless interactions with fixed-position wireless field devices can be achieved. Finally, while the various methods provided for obtaining the position of handheld field maintenance tool 52 are described above, they can also be used in conjunction with one another to provide additional accuracy and/or redundancy. Additionally, tool 52 also preferably comprises compass module 152 coupled to controller 130 such that tool 52 can indicate the compass direction in which it is pointing. Finally, tool 52 can also include tilt module 154 coupled to controller 130 to provide an indication to controller 130 relative to an angle of inclination of tool 52 relative to gravity. However, additional axes of sensing are also contemplated.

As illustrated in FIG. 3, handheld field maintenance tool 52 preferably includes camera 157. Camera 157 is preferably disposed within handheld field maintenance tool 52, and is configured to acquire still and/or video images. Further, camera 157 can also be provided with an audio input such that real-time video recording with sound can be provided.

Virtually all of the communication and interaction between handheld field maintenance tool 52 and any field devices is performed based upon an understanding, or analysis of the field device's Electronic Device Description (EDD). An Electronic Device Description is an exhaustive listing of the functions, parameters, methods, and menus that can be used in conjunction with the individual field device. Accordingly, an EDD is generally created by the manufacturer of a field device. An EDD is written in a human-readable Electronic Device Description Language (DDL) that sets forth a structure and manner for describing the data available from the field device, the meaning of the data associated with the field device, the methods available for execution by the field device, the format of communicating with the field device, and an exhaustive listing of user interface information about field device such that various displays and menus can be generated, or otherwise rendered to a user.

An Electronic Device Description Language source file, in human-readable form, is generally compiled into a binary file to produce a machine-readable file that is simply known as an Electronic Device Description. It is this Electronic Device Description that is then employed by the handheld field maintenance tool to interact with the field device in accordance with the Electronic Device Description. One manner of such interaction includes the generation and rendering of menus on display 120 based upon Electronic Device Description menu information relative to a specific field device. For a simple field device, the menu may be very simple such as indicating diagnostic test, or providing a function of replacing a sensor. However, modern field devices generally perform a significant amount of operations in conjunction with diagnostics, mathematical analysis of process variables, and configuration. Thus, menus for modern field devices are already quite complex, and growing more complex as new features and functions are provided. For example, even with Electronic Device Descriptions written with Human Centered Design principles in mind, it has been found that lists of tasks with numeric keys sequences (known as fast keys) are simpler for users to understand. For example, if a user wishes to modify the tag in a pressure transmitter sold by Emerson Process Management, such as a 3051 Rev. 7, Device Description Rev. 9, the fast key sequence described by the manufacturer tells the user to press keys 2,2,5,1. The fast key number corresponds to menu lines in the Electronic Device Description, and pressing the number on a keypad of the handheld field maintenance device selects the menu items. However, the user must still be able to access the quick installation guide or find the fast key sequence from some other suitable location. Moreover, the user must still press the correct key numbers in order to do the desired task.

For reference, Table 1 below provides fast keys for "Fully Compensated Mass and Energy Flow" available from a Model 3051 SMV Pressure Transmitter available from Emerson Process Management of Chanhassen, Minn.

| FUNCTION | FAST KEY SEQUENCE |
| --- | --- |
| Differential Pressure Units | 1, 3, 3, 4 |
| Energy Rate Units | 1, 3, 3, 2 |
| Energy Reading and Status | 1, 4, 2, 1, 2 |
| Equipped Sensors | 1, 4, 4, 4 |
| Field Device Information | 1, 4, 4, 1 |
| Flow Calculation Type | 1, 4, 1, 1, 2 |
| Flow Rate Units | 1, 3, 3, 1 |
| Flow Reading and Status | 1, 4, 2, 1, 1 |
| Gage Pressure Reading and Status | 1, 4, 2, 1, 6 |
| Gage Pressure Sensor Limits | 1, 4, 1, 5, 9 |
| Gage Pressure Units | 1, 3, 3, 6 |
| LCD Configuration | 1, 3, 8 |
| Loop Test | 1, 2, 2 |
| Module Temperature Reading and Status | 1, 4, 2, 1, 8 |
| Module Temperature Units | 1, 3, 3, 8 |
| Poll Address | 1, 4, 3, 3, 1 |
| Process Temperature Reading and Status | 1, 4, 2, 1, 7 |
| Process Temperature Sensor Mode | 1, 4, 1, 6, 8 |
| Process Temperature Sensor Trim Options | 1, 2, 5, 5 |
| Process Temperature Unit | 1, 3, 3, 7 |
| Ranging the Analog Output | 1, 2, 5, 1 |
| Recall Factory Trim Settings | 1, 2, 5, 2, 3 |
| Sensor Information | 1, 4, 4, 2 |
| Static Pressure Sensor Lower Trim (AP Sensor) | 1, 2, 5, 4, 2 |
| Static Pressure Sensor Trim Options | 1, 2, 5, 4 |
| Static Pressure Sensor Zero Trim (GP Sensor) | 1, 2, 5, 4, 1 |
| Status | 1, 2, 1 |
| Tag | 1, 3, 1 |
| Test Flow Calculation | 1, 2, 3 |
| Totalizer Configuration | 1, 4, 1, 3 |
| Totalizer Reading and Status | 1, 4, 2, 1, 3 |
| Totalizer Units | 1, 3, 3, 3 |
| Variable Mapping | 1, 4, 3, 4 |
| Write Protect | 1, 3, 5, 4 |

Table 2 provides yet another listing of fast keys for "Direct Process Variable Output."

| FUNCTION | FAST KEY SEQUENCE |
| --- | --- |
| Absolute Pressure Reading and Status | 1, 4, 2, 1, 2 |
| Absolute Pressure Sensor Limits | 1, 4, 1, 2, 8 |
| Absolute Pressure Units | 1, 3, 3, 2 |
| Alarm and Saturation Level Configuration | 1, 4, 2, 6, 6 |
| Alarm and Saturation Levels | 1, 4, 2, 6 |
| Analog Output Trim Options | 1, 2, 4, 2 |
| Burst Mode Setup | 1, 4, 3, 3, 3 |
| Burst Mode Options | 1, 4, 3, 3, 4 |
| Callendar-van Dusen Sensor Matching | 1, 2, 4, 5, 4 |
| Damping | 1, 3, 7 |
| Diaphragm Seals Information | 1, 4, 4, 4 |
| Differential Pressure Reading and Status | 1, 4, 2, 1, 1 |
| Differential Pressure Sensor Trim Options | 1, 2, 4, 3 |
| Differential Pressure Zero Trim | 1, 2, 4, 3, 1 |
| Differential Pressure Units | 1, 3, 3, 1 |
| Equipped Sensors | 1, 4, 4, 3 |
| Field Device Information | 1, 4, 4, 1 |
| Gage Pressure Reading and Status | 1, 4, 2, 1, 3 |
| Gage Pressure Sensor Limits | 1, 4, 1, 2, 9 |
| Gage Pressure Units | 1, 3, 3, 3 |
| LCD Configuration | 1, 3, 8 |
| Loop Test | 1, 2, 2 |
| Module Temperature Reading and Status | 1, 4, 2, 1, 5 |
| Module Temperature Units | 1, 3, 3, 5 |
| Poll Address | 1, 4, 3, 3, 1 |
| Process Temperature Reading and Status | 1, 4, 2, 1, 4 |
| Process Temperature Sensor Trim Options | 1, 2, 4, 5 |
| Process Temperature Units | 1, 3, 3, 4 |
| Ranging the Analog Output | 1, 2, 4, 1 |
| Recall Factory Trim Settings | 1, 2, 4, 2, 3 |
| Sensor Information | 1, 4, 4, 2 |
| Static Pressure Sensor Lower Trim (AP Sensor) | 1, 2, 4, 4, 2 |
| Static Pressure Sensor Trim Options | 1, 2, 4, 4 |
| Static Pressure Sensor Zero Trim (GP Sensor) | 1, 2, 4, 4, 1 |
| Status | 1, 2, 1 |
| Tag | 1, 3, 1 |
| Transfer Function | 1, 3, 6 |
| Variable Mapping | 1, 4, 3, 4 |
| Write Protect | 1, 3, 5, 4 |

As set forth in Tables 1 and 2 above, the natural language description of a user-desired task is essentially provided with a sequence of keys that will quickly allow the user or technician to execute that task. Given that EDD menus, and accordingly fast key sequences, will likely vary for each and every model of field device available from a given manufacturer, and certainly among those from different manufacturers, there is really nothing that a technician can effectively memorize. Thus, a technician would need to maintain a copy of a quick installation guide, or equivalent document, relative to each and every field device that he or she would be interacting with in order to employ fast key sequences for those devices.

Figure 4:
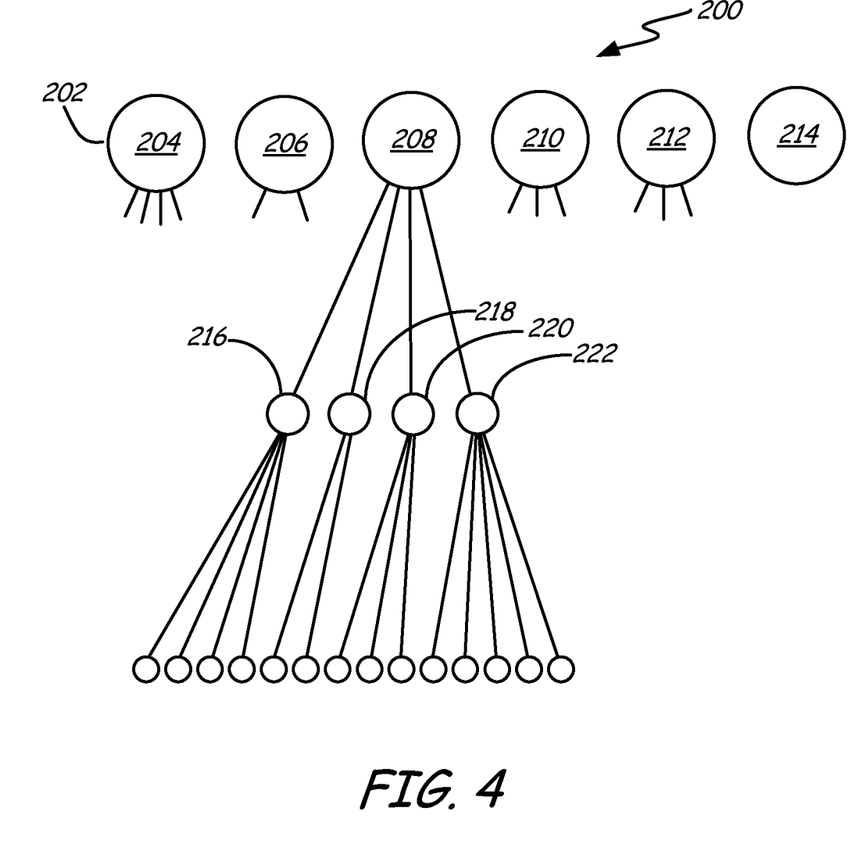
FIG. 4 is a diagrammatic view illustrating a representative menu hierarchy illustrative of the type used in Device Descriptions in accordance with an embodiment of the present invention.

FIG. 4 is a diagrammatic view illustrating a representative menu hierarchy illustrative of the type used in EDDs. Menu 200 has a first level 202 within which six distinct options 204, 206, 208, 210, 212, and 214 are available. Each such option generally has a number of sub-menus. For simplification of the figure, only the sub-menus for menu item 208 are illustrated in FIG. 4. Menu item 208, if selected, will present the user with four distinct sub-menu options. Specifically, sub-menu options 216, 218, 220, and 222 are provided. Further still, each such sub-menu item has further sub-menu items, et cetera. While menu items and descriptions are generally intuitive, and help facilitate a user's navigation therethrough to arrive at an endpoint that executes a desired task, the user's initial conception of a task will generally not be specifically enumerated in the first level, 202, menu items. Instead, a more general description of a type of task that might accord with the user's conceptual task would be provided. The user would still need to traverse the menu tree to hopefully arrive at the selected task. Accordingly, fast keys allow the user to begin with a specific task in mind, and enter menu keys into the handheld field maintenance tool to quickly arrive at an endpoint.

In accordance with the embodiment of the present invention, an automated computer-implemented method is provided whereby the user of the handheld field maintenance device can easily access a quick installation guide directly on the handheld field maintenance tool for the purpose of finding the fast key sequences, and even selecting the task directly. The data from the fast key sequence tasks, as set forth in the quick installation guide, is preferably encoded into a machine-readable file that is included with the Device Description when the user loads the Device Description onto the handheld field maintenance tool. This additional encoded file is invoked, or otherwise employed, when the user connects the handheld field maintenance tool to a supported field device (for which the auxiliary encoded file is provided), and an icon on the display screen of the handheld field maintenance tool will indicate that automatic fast key sequence tasks are available for that field device. The technician, or user may then invoke the fast key sequence menu on the handheld field maintenance tool, and an application on the tool will display all tasks available to the user. The user may search among the tasks for a keyword, such as "calibration", or may simply browse and select a specific task from all tasks. When the user selects the task, the handheld field maintenance tool will automatically traverse the EDD menu tree in accordance with the encoded fast key sequence. Thus, the user or technician does not even have to enter the fast key sequence. Instead, the user must only select the task from the list generated in the processing of the quick installation guide.

Figure 5:
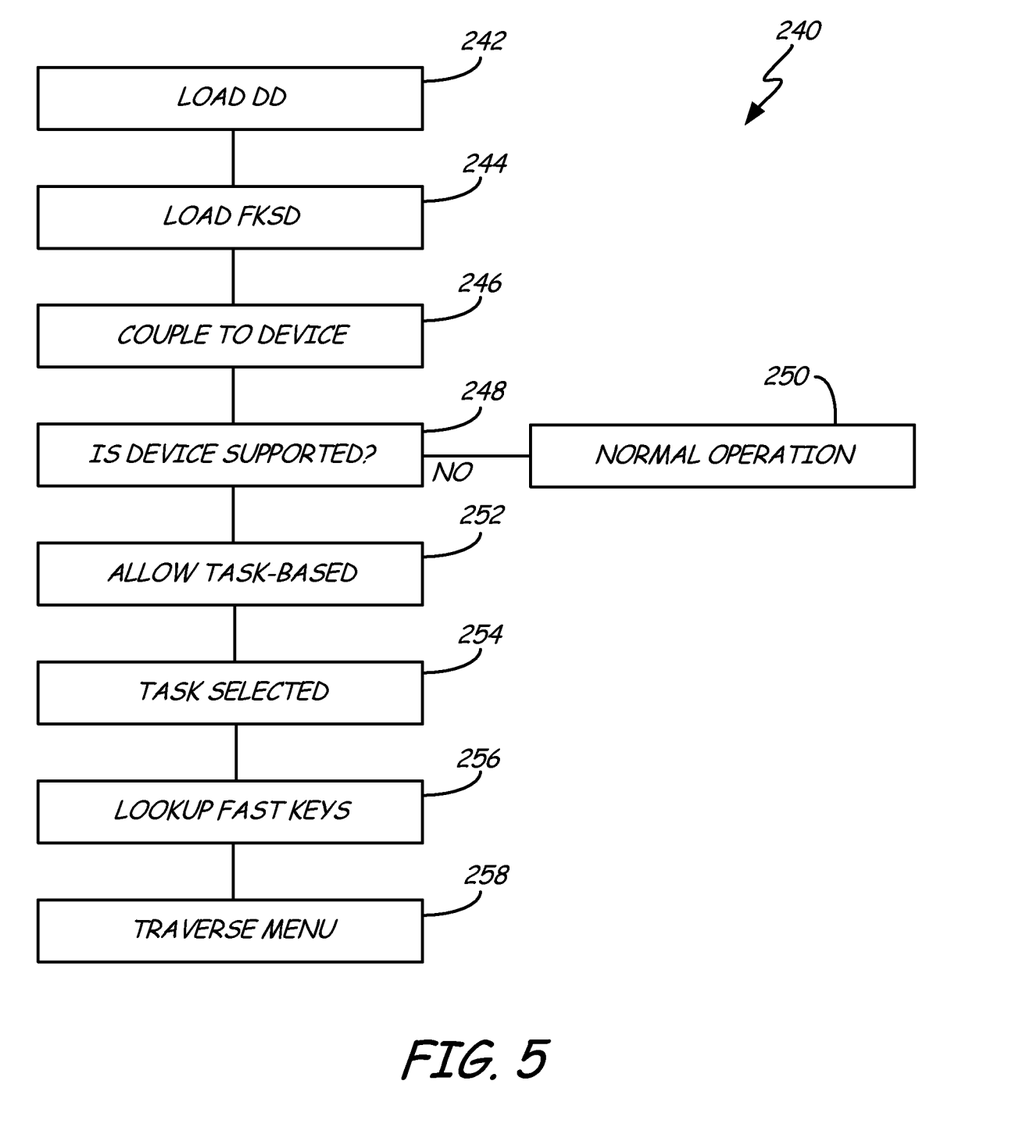
FIG. 5 is a flow diagram of a method of providing task-based field maintenance using a handheld field maintenance tool in accordance with an embodiment of the present invention.

FIG. 5 is a flow diagram of a method of providing task-based field maintenance using a handheld field maintenance tool in accordance with an embodiment of the present invention. Method 240 begins at block 242 where at least one EDD is loaded into the handheld field maintenance tool. At block 244, fast key sequence data relative to one or more field devices is also loaded into the handheld field maintenance tool. Note, blocks 242 and 244 may be combined if Electronic Device Description Language permits, or is modified to permit the description of tasks relative to fast key sequences. Moreover, while blocks 242 and 244 are generally performed with respect to at least one field device, memory technology is progressing to such an extent that blocks 242 and 244 may, in fact, be executed for all commercially available field devices. At block 246, the handheld field maintenance tool is communicatively coupled to a field device. When such coupling occurs, the handheld field maintenance tool determines the type of field device to which it is connected, and further determines whether fast key sequence data is available for the coupled field device, as indicated at block 248. If no fast key sequence data is available, control passes to block 250 and operation occurs normally, and is not augmented with task-based field maintenance. However, if fast key sequence data is available for the coupled field device, control passes to block 252 where task-based field maintenance is permitted. An indication is preferably provided to the user or technician by virtue of the display of a menu icon, audible alert, or other suitable indicator that task-based field maintenance is enabled. If the user or technician indicates that he or she wishes to perform a task-based field maintenance operation, control passes to block 254 where task selection occurs. As set forth above, task selection may be performed in any number of ways. For example, the user may be presented with a text box which may receive one or more keywords to allow the user to search among the various tasks to potentially locate a desired task. However, task selection can occur by simply allowing the user to browse all available tasks and select one. Once a task is selected at block 254, method 240 causes the controller 130 of the handheld field maintenance tool to lookup, or otherwise access the fast key sequence data relative to the selected task, as indicated at block 256. Once such data has been accessed, the handheld field maintenance tool automatically traverses the field device's menu in accordance with the fast key sequence data much as if the user had actually entered the fast key sequence data into the numeric keypad itself. This is indicated at block 258.

Figure 6:
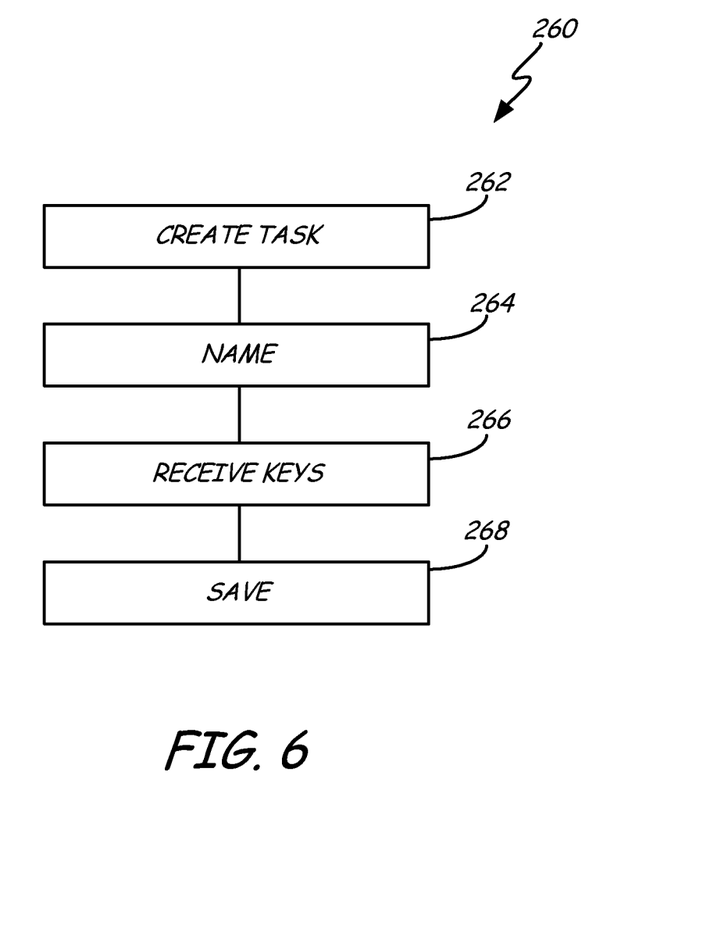
FIG. 6 is a flow diagram of a method of creating a user-generated task in accordance with an embodiment of the present invention.

FIG. 6 is a flow diagram of a method of creating a user-generated task in accordance with an embodiment of the present invention. Method 260 begins at block 262 where a user indicates a desire to create a task. This can be as simple as pressing a "Create Task" button on the handheld field maintenance tool, on display 120 (in embodiments where display 120 is a touchscreen) or any other suitable method. Method 260 continues at block 264 where the user enters a name or natural-language description of the task to be entered. Next, at block 266, the user enters a sequence of keys which traverses the menu tree of a particular field device, in order to execute a function associated with the task. Finally, at block 268, the task is saved. If the handheld field maintenance tool is coupled to a field device at the time, an association between the field device and the user-created task can be stored locally on the handheld field maintenance tool to be executed later, and/or uploaded to an external device such as an asset management system, et cetera. Additionally, the user-created task may also be associated with the type of field device which is coupled to the handheld field maintenance tool. In this manner, the user-created task can be executed on other field devices that share the device type. If no field device is coupled to the handheld field maintenance tool when the task is created, the user can be prompted to select a field device, preferably among all field devices for which EDDs are currently stored in the handheld field maintenance tool (for association with the newly-created task).

While embodiments of the present invention thus far have generally facilitated user interaction with the sometimes cumbersome menu structure of field devices based upon desired tasks, another improvement specifically facilitates the user's traversal of the menu tree itself. As indicated in FIG. 2, the physical display size of a handheld field maintenance tool is relatively limited. Moreover, to date, when a user is interacting upon a certain menu level, such as menu level 202 illustrated in FIG. 4, only menu items of that particular level are displayed to the user. For example, if the user is interacting on menu level 202, only items 204, 206, 208, 210, 212, and 214 will be displayed. This can make it difficult for the user or technician to know where they are relative to the entire menu tree. Further, the user may not know where, in the menu tree, they have come from, and how many more levels it will be before they arrive at the particular menu endpoint that they desire. Often, the user manual for the field device with which the user is working will have the complete (or nearly complete) menu. This is often referenced by the user as it clearly shows the user where, in the menu tree, they need to be. However, since the handheld field maintenance tool can only display one menu level at a time, it can still sometimes be difficult to determine the path needed to take to arrive at an endpoint in the menu tree.

Figure 7:
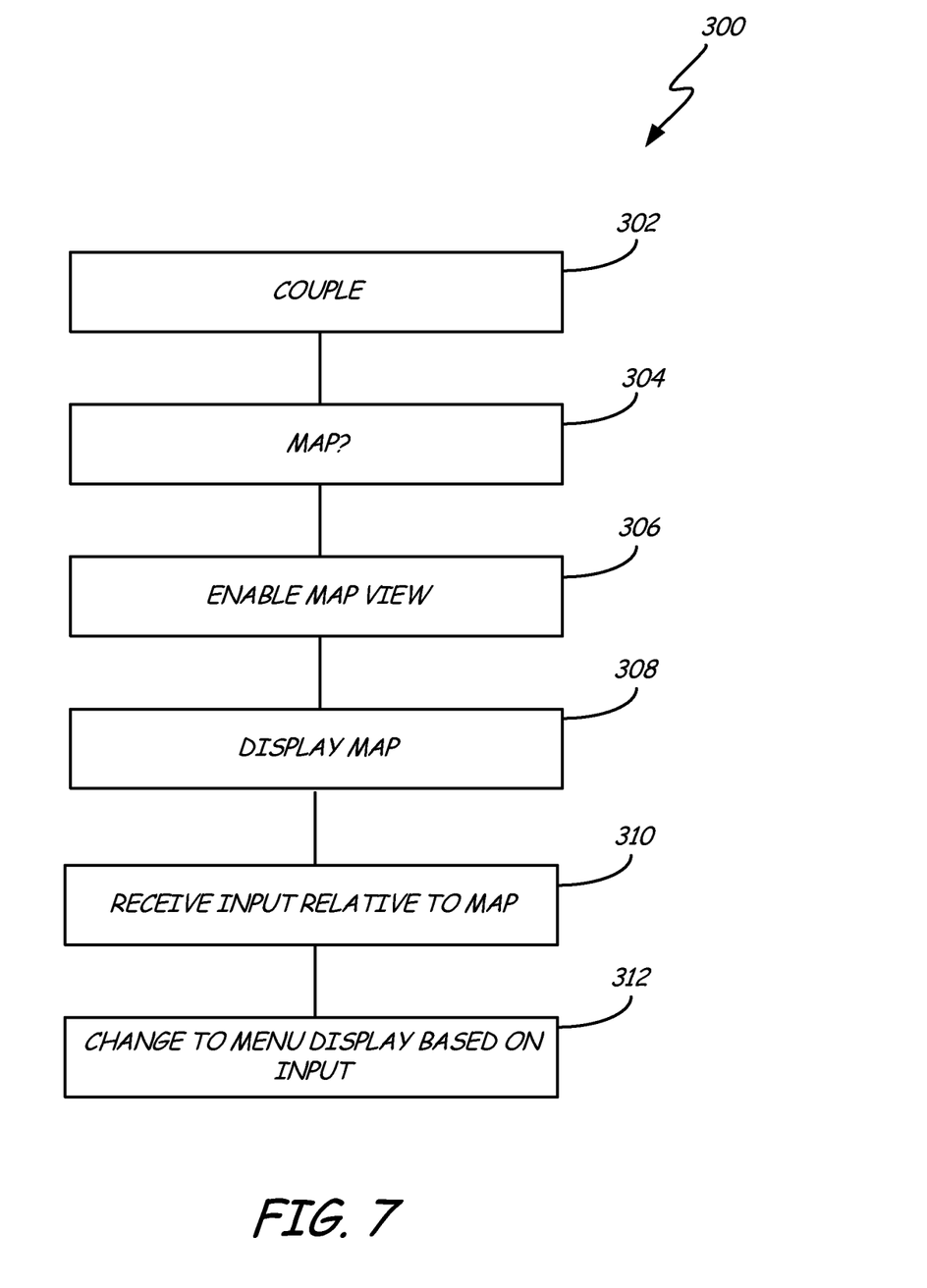
FIG. 7 is a flow diagram of a method of providing a menu map on a handheld field maintenance tool in accordance with an embodiment of the present invention.

FIG. 7 is a flow diagram of a method of providing a menu map on a handheld field maintenance tool in accordance with an embodiment of the present invention. Method 300 begins at block 302 where a handheld field maintenance tool is communicatively coupled to a field device. When the handheld field maintenance tool first communicates with a field device, the handheld field maintenance tool determines if it has a map available for the menu of the field device, as indicated at block 304. As used herein, a map is a substantially pictorial representation of a field device's menu structure. The map may be a separate image file that is provided along with an EDD, or it can be an image that is generated by the handheld field maintenance tool by analyzing, or otherwise parsing, an EDD file for a field device. If such map is available, an icon, to this effect, may be displayed on the handheld field maintenance tool display 120, indicating that map view is enable as shown at block 306. If the icon is selected by the user, the handheld field maintenance tool display will change from the standard menu view to a map view, as indicated at block 308. As set forth above, field device menus are relatively complex, and growing more so. Accordingly, in some embodiments, the entire menu map may not fit in display 120 and still be legible. Preferably, colors and/or shapes of icons can be used to identify certain types of tasks, or features available within the map. The handheld field maintenance tool receives input that causes the entire menu map to be manipulated, such as zoomed, panned, or translated up/down to obtain the desired resolution and location. This would be similar to the way that a user interacts with a geographical map on, for example, a smart phone. Once the user or technician has arrived at a desired location within the menu map itself, the user may select a portion of the map that they need, as indicated at block 310. Upon selecting the portion, the handheld field maintenance tool will switch back to the standard menu view where the user can finish the desired task, as indicated at block 312. Preferably, when the user has finished the desired task, the map icon is still available such that the user can revert back to the interactive map. In this way, a user can move among multiple levels within the menu hierarchy in a manner that is fast and intuitive.

Although the present invention has been described with reference to particular embodiments, workers skilled in the art will recognize that changes may be made in form and detail without departing from the spirit and scope of the invention.

What is claimed is:

1. A computer-implemented method for creating a task-based field maintenance operation using a handheld field maintenance tool, the method comprising:
   communicably coupling the handheld field maintenance tool to a field device;
   detecting that a set of automatic fast-key sequences is available for the field device;
   providing an indication that the automatic set of fast-key sequences is available for the field device;
   receiving a user input to correlate a selected task-based field maintenance operation, implemented on a handheld field maintenance tool, to one of the fast-key sequences;
   receiving a user-generated label for the selected task-based field maintenance operation;
   receiving a plurality of keystrokes on the handheld field maintenance tool specific to the user-generated label and specific to the selected task-based field maintenance operation;
   linking the user-generated label to the selected task-based field maintenance operation using the plurality of keystrokes; and
   storing information indicative of the user-generated label in an Electronic Device Description (EDD) menu of an EDD, and the plurality of keystrokes and the selected task-based field maintenance operation in a guide of the EDD, and adding the plurality of keystrokes to the set of automatic fast-key sequences such that a user selection of the user-generated label causes the handheld field maintenance tool to automatically traverse the EDD menu to implement the selected task-based field maintenance operation.

2. The method of claim 1, and further comprising obtaining a device type for the field device, and associating the task-based field maintenance operation with the device type.

3. The method of claim 1, and further comprising uploading the stored information indicative of the user-generated label and the user-generated plurality of keystrokes to another device.

4. The method of claim 1, and further comprising:
   receiving user input of the user-generated plurality of keystrokes selecting the task-based field maintenance operation; and
   generating a series of signals to the field device corresponding with the stored user-generated plurality of keystrokes.

* * * * *